United States Patent [19]

Szilágyi et al.

[11] 4,224,325
[45] Sep. 23, 1980

[54] 3-(1-PYRAZOLYL)-PYRIDAZINE DERIVATIVES AND HYPOTENSIVE COMPOSITIONS THEREOF

[75] Inventors: Géza Szilágyi; Endre Kasztreiner; László Tardos; Edit Kósa; László Jaszlits; György Cseh; Ilona Kovács, nee Szabó; Pál Tolnay; Sándor Elek; István Elekes; István Polgari, all of Budapest, Hungary

[73] Assignee: Richter Gedeon Vegyészeti Gyár Rt., Budapest, Hungary

[21] Appl. No.: 923,623

[22] Filed: Jul. 11, 1978

[30] Foreign Application Priority Data

Oct. 25, 1977 [HU] Hungary ............................ GO 1381

[51] Int. Cl.³ ................ C07D 403/04; C07D 413/14; A61K 31/50; A61K 31/535
[52] U.S. Cl. .............................. 424/250; 424/248.4; 424/248.56; 424/248.57; 544/238; 544/114
[58] Field of Search ............... 544/238, 114; 424/250, 424/248.56, 248.57, 248.4

[56] References Cited

PUBLICATIONS

Berger et al., Chem. Abs. 81, 120674s (1974).
Elguerdo et al., Bull. Soc. Chem. Fr. 1970, 1346.
Shirakawa et al., Chem. Abs. 60, 12009 (1964).
Twomey, Chem. Abs. 81, 3870t (1974).

*Primary Examiner*—Mark L. Berch
*Attorney, Agent, or Firm*—Karl F. Ross

[57] ABSTRACT

The invention relates to compounds of general formula

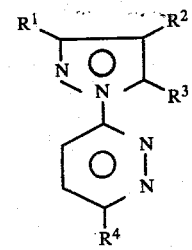

wherein
$R^1$ stands for a hydrogen atom or a $C_{1-6}$ alkyl-, a $C_{2-4}$ hydroxyalkyl, a $C_{3-6}$ cycloalkyl or a phenyl group,
$R^2$ stands for a hydrogen, fluorine, chlorine or bromine atom or a $C_{1-6}$ alkyl, a $C_{2-4}$ hydroxyalkyl, a nitro or an $-NR^5R^6$ group, wherein $R^5$ and $R^6$ may have the same or different meaning and stand each for a hydrogen atom or a $C_{1-4}$ alkyl or a $C_{2-4}$ hydroxyalkyl group,
$R^3$ stands for a hydrogen atom or a $C_{1-6}$ alkyl, a $C_{2-4}$ hydroxyalkyl, a $C_{3-6}$ cycloalkyl or a phenyl group, a chlorine atom or a hydroxyl, amino or methoxy group,
$R^4$ stands for a carbamoyl, a cyano or an $-NR^7-NHR^8$ group, wherein $R^7$ and $R^8$ may have the same or different meaning and stand each for a hydrogen atom or a $C_{1-4}$ alkyl, a $C_{2-4}$ hydroxyalkyl, a $C_{1-4}$ alkoxycarbonyl or an $-NR^9R^{10}$ group, wherein $R^9$ and $R^{10}$ may have the same or different meaning and stand each for a hydrogen atom or a $C_{1-5}$ alkyl, a $C_{2-4}$ hydroxyalkyl, a $C_{3-6}$ cycloalkyl, a phenyl or a benzyl group, or $-NR^9R^{10}$ may represent a morpholine, piperidine or piperazine ring, and their pharmaceutically acceptable acid-addition salts. Furthermore, the invention relates to a process for preparing these compounds.

The novel compounds of general formula I have valuable pharmacological properties. Thus they show a considerable hypotensive effect and are capable to inhibit enzymes regulating the catabolism of prostaglandins.

12 Claims, No Drawings

3-(1-PYRAZOLYL)-PYRIDAZINE DERIVATIVES AND HYPOTENSIVE COMPOSITIONS THEREOF

FIELD OF THE INVENTION

This invention relates to novel 3-(1-pyrazolyl)-pyridazine derivatives and to their pharmaceutically acceptable salts and to composition containing these compounds.

BACKGROUND OF THE INVENTION

It is well known that one of the most dangerous hypertensive conditions is renal hypertension arising from renal insufficiency which is characterized, on the one hand, by constriction of the blood vessels of kidney and, on the other hand, according to recent investigations, by a decreased prostaglandin content of blood vessel walls of the kidney (Circ. Res. 36–37, Suppl. I, pp. 68 and 81, 1975) which is closely related to the process of constriction of the blood vessels of kidney.

DESCRIPTION OF THE INVENTION

Now it has been found that the 3-(1-pyrazolyl)-pyridazine compounds of formula I (below) possess considerable hypotensive effect and are capable of significantly inhibiting enzymes (prostaglandin dehydrogenase and prostaglandin-A isomerase) regulating the catabolism of prostaglandins, thereby giving an increase in the endogenous prostaglandin levels.

Accordingly the invention relates to 3-(1-pyrazolyl)-pyridazine derivatives of the formula I

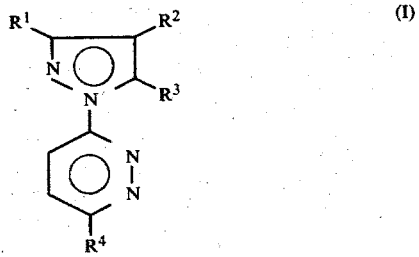
(I)

wherein
$R^1$ is hydrogen, $C_{1-6}$ alkyl, $C_{2-4}$ hydroxyalkyl, $C_{3-6}$ cycloalkyl or phenyl,
$R^2$ is hydrogen, fluorine, chlorine or bromine or $C_{1-6}$ alkyl, $C_{2-4}$ hydroxyalkyl, nitro or $-NR^5R^6$, wherein $R^5$ and $R^6$ are the same or different and each is hydrogen or a $C_{1-4}$ alkyl or $C_{2-4}$ hydroxyalkyl,
$R^3$ is hydrogen or $C_{1-6}$ alkyl, $C_{2-4}$ hydroxyalkyl, $C_{3-6}$ cycloalkyl or phenyl, chlorine or hydroxyl, amino or methoxy,
$R^4$ is carbamoyl, cyano or $-NR^7-NHR^8$, wherein $R^7$ and $R^8$ are the same or different and each is hydrogen or a $C_{1-4}$ alkyl, $C_{2-4}$ hydroxyalkyl, $C_{1-4}$ alkoxycarbonyl or $-NR^9R^{10}$, wherein $R^9$ and $R^{10}$ are the same or different and each is hydrogen or $C_{1-5}$ alkyl, $C_{2-4}$ hydroxyalkyl, $C_{3-6}$ cycloalkyl, phenyl or benzyl, or $-NR^9R^{10}$ represents a morpholine, piperidine or piperazine ring,
and their pharmaceutically acceptable acid-addition salts.

In the compounds of formula I, $R^1$ preferably is hydrogen or methyl, ethyl, isopropyl or cyclopropyl, whereas $R^2$ is preferably hydrogen or chlorine, or nitro or amino, and $R^3$ preferably is methyl, ethyl, isopropyl, cyclopropyl or amino, whereas $R^4$ is preferably hydrazino, morpholino or bis(hydroxyethyl)-amino.

The compounds of formula I can be prepared according to the invention by one of the steps of
(a) by reacting a compound of formula II

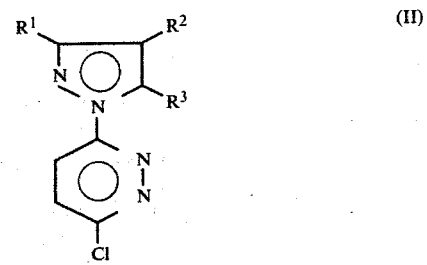
(II)

with a hydrazine of the formula $NHR^7-NHR^8$, or with an amine of the formula $NHR^9R^{10}$;

(b) for compounds of the formula I, wherein $R^2$ is $-NR^5R^6$, by reducing a compound of formula III

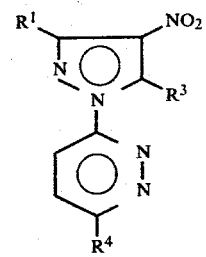

and, if desired, subjecting to hydrolytic decarboxylation the thus-obtained compound of formula I, wherein $R^2$ is amino and $R^4$ is $-NR^7-NHR^8$, one of whose substituents $R^7$ and $R^8$ is a $C_{1-4}$ alkoxycarbonyl group while the other is hydrogen and, if desired, by alkylating the compound; and (c) by reacting a compound of formula IV

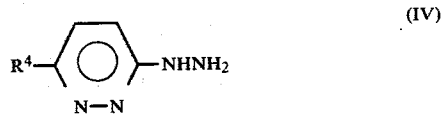
(IV)

with a compound of formula V

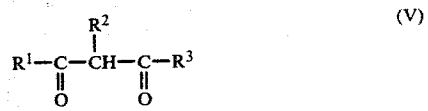
(V)

or formula VI

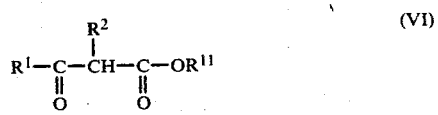
(VI)

or formula VII

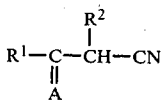

(VII)

wherein R[11] is $C_{1-4}$ alkyl group, whereas A is oxygen atom or an —NH group, and, if desired, reacting the thus-obtained compound of formula I, with a chlorinating or methylating agent.

If desired, the thus-obtained free base of formula I is converted into a pharmaceutically acceptable acid-addition salt, or a corresponding acid addition-salt is converted into the free base.

The compounds of formula II are preferably transformed into the compounds of formula I by a step in which a chloro derivative of formula II is reacted with an excess of a hydrazine of the formula $NHR^7$—$NHR^8$ or with an excess of an amine of the formula $HNR^9R^{10}$ with or without solvents, advantageously at a temperature between 50° C. and 180° C. As solvents, polar liquids, e.g. lower aliphatic alcohols, dimethyl formamide or dimethyl sulphoxide, are preferably used.

For the preparation of the compounds of the formula II, 3-chloro-6-pyridazinylhydrazine is a suitable starting material. Compounds of formula II, wherein $R^2$ is hydrogen, $C_{1-6}$ alkyl or $C_{2-4}$ hydroxyalkyl and where $R^3$ is not chlorine or methoxy, can suitably be prepared by reacting 3-chloro-6-pyridazinylhydrazine with a 2-$R^2$-1,3-propandione or beta-ketoester or beta-keto(or imino) nitrile with or without a solvent. Lower aliphatic alcohols are preferably used as solvents, at a temperature between 50° C. and 100° C.

The compounds of formula II, wherein $R^2$ is fluorine, chlorine or bromine can advantageously be prepared by reacting compounds of the formula II, wherein $R^2$ is hydrogen with the corresponding halogen or halogen-carrier agent, e.g. sulphuryl chloride, suitably at a temperature between 50° C. and 150° C. The use of a halogenated hydrocarbon, e.g. chloroform or carbon is tetrachloride, as solvent is quite convenient in this reaction.

The compounds of formula II, wherein $R^2$ is can be prepared by nitration of the compounds of formula II, wherein $R^2$ is hydrogen, by means of nitrating acid or a mixture of nitric acid and acetic acid, preferably at a temperature between 0° C. and 50° C.

The compounds of formula II, wherein $R^2$ is amino, can conveniently be prepared by dephthaloylation of the corresponding phthalimido compounds with hydrazine, the reaction being carried out preferably in a lower aliphatic alcohol as solvent, at temperature of the boiling point.

The compounds of formula II, wherein $R^2$ is fluorine, can conveniently be prepared via the Sandmeyer's reaction, i.e. by reacting with ammonium fluoborate the diazonium salts obtained through diazotation from the corresponding amino compound and by tranforming the thus-obtained fluoborate to the fluoro derivative by thermal decomposition.

The compounds of formula II, wherein $R^3$ is chlorine atom, are conveniently prepared by reacting a compound of the formula II wherein $R^3$ is hydroxyl with a chlorinating agent, e.g. with phosphorus oxychloride, phosphorus pentachloride or a mixture, thereof preferably at a temperature between 30° C. and 120° C., in some cases in the presence of an acid binding agent, e.g. a tertiary amine, such as dimethyl aniline.

The compounds of formula II wherein $R^3$ is methoxy, are conveniently prepared by methylating a compound of formula II wherein $R^3$ is hydroxyl, with a methylating agent, e.g. methyl iodide or methyl sulphate, advantageously at a temperaure between 10° C. and 100° C., in a polar solvent, e.g. dimethyl formamide or dimethyl sulphoxide.

The transformation of compounds of formula III to the compounds of formula I can be achieved with reducing a compound of formula III catalytically or in some cases by stannous chloride. The reduction is conveniently carried out with a palladium on charcoal catalyst in a lower aliphatic alcohol as solvent at a temperature between 10° C. and 40° C.

Reaction of the compounds of formula IV with the compounds of formula V, VI or VII can suitably carried out by heating the components together in lower aliphatic alcohols or ethers, e.g. in ethyl or tetrahydrofurane, as solvents, preferably at a temperature between 10° C. and 100° C. In some cases the use of an organic base as nucleophilic catalyst is advantageous.

Of the compounds of formula IV, 3-carbamoyl-6-pyridazinylhydrazine (Bull. Soc. Chem. France 1959, 1973), 3-cyano-6-pyridazinylhydrazine (Hungarian patent specification No. 165,304) and pyridazinylhydrazines substituted by amino group (e.g. J. Med. Chem. 18, 741, 1975) are known in the literature. Preparation of pyridazinylhydrazines that are unknown are described in the Examples.

A large number of the compounds of general formula V are known in the literature. These can be in general simply prepared by the mixed Claisen's condensation of the properly substituted methyl ketone with a carboxylic acid ester (e.g. Tetrahedron 26, 4691, 1970) or H. Gilman: Org. Synth., I, 78 and 205, 1951, John Wiley and Sons, London) and some are commereially available (e.g. acetyl acetone or malondialdehyde in the tetraacetal form). The 1,3-propanediones unknown in the literature are described in the Examples.

The beta-ketoesters of formula VI are in known in the literature and can be prepared either by the Grignard reaction of cyanoacetic acid esters or by the alkoxycarbonylation of methyl ketones (e.g. J. Amer. Chem. Soc. 63, 2252 1941 and 67, 2197 1945). Some of them, e.g. the esters of aceto acetic acid, are commercially available.

Many of the compounds of formula VII are known in the literature. Thus e.g. 2-iminobutyronitrile can be prepared by the autocondensation of acetonitrile in the presence of sodium (J. Amer. Chem. Soc. 64, 152, 1942) and benzoylacetonitrile can be prepared by the benzoylation of acetonitrile (J. Amer. Chem. Soc. 69, 990, 1947).

The compounds of formula I wherein $R^4$ is —NH-7—$NHR^8$ and $R^7$ and $R^8$ each stand for a $C_{104}$ alkoxycarbonyl group, can also be synthesized by reacting a hydrazine compound of formula I wherein $R^4$ is hydrazino with the proper alkyl chloroformate or diethyl pyrocarbonate, suitably at a temperature between 0° C. and 120° C., in a halogenated hydrocarbon as solvent, e.g. in dichloromethane or in pyridine which acts simultaneously as an acid binding agent.

The acid-addition salts of the compounds of formula I can conveniently be prepared in the following way. The base of formula I is dissolved, e.g. in methanol, ethanol, isopropanol or ether, and to this solution the solution of the desired inorganic acid in methanol, ethanol or ether or a solution of the desired organic acid in methanol, ethanol, isopropanol, ether or acetone, respectively, is added dropwise under cooling. The precipitated product can be separated by filtration and recrystallized, if desired.

Hydrochloric, hydrobromic, sulphuric or phosphoric acid can conveniently be used as inorganic acids. The use of tartaric, maleic, fumaric, methanesulphonic, ethanesulphonic or 4-toluenesulphonic acid is suitable as organic acids.

The hyrotensive action of the compounds according to the invention was demonstrated in cats of both sexes weighing 2 to 4 kg, narcotized intraperitoneally by 30 mg/kg of Pentobarbital (5-ethyl-5-(1-methyl-butyl)-barbituric acid( L. A. Geddes: The Direct and Indirect Measurement of Blood Pressure, Year Book Medical Publishers, Chicago, 1970). The substances were administered in doses of 5, 2.5 and 1 mg/kg, respectively, and Hydralazine (1-hydrazinophthalazine hydrochloride) was used as a reference compound. The hypotensive action of several substances is shown in Table I.

Table I

| No.of Example | Decrease in blood pressure in Hgmm by 1 mg/kg | Acute oral toxicity on mice $LD_{50}$ in mg/kg |
| --- | --- | --- |
| 25 | −30 | 200 |
| 26 | −40 | 100 |
| 29 | −40 | ~150 |
| 31 | −15 | 100 |
| 34 | −20 | >200 |
| 40 | −30 | 200 |
| 44 | ″40 | >200 |
| 45 | −30 | 200 |
| 46 | −50 | 200 |
| 56 | −35 | 200 |
| Hydralazine | −40 | 200 |

The hypotensive action of substance 44 was studied also in spontaneously hypertensive (Wistar-Okamoto(-rats)Arzneim.- forsch. 6, 222, 1956): the systolic blood pressure was measured in the caudal artery by an indirect method, after oral treatment. Substance 44, when administered in a dose equal to Hydralazine, showed the same effectivity together with the same duration of effect. Highly advantageous properties against Hydralazine of substance 44 are its extraordinarily favorable toxicity and inability to cause tachycardia. Further advantages are provided, firstly in the case or renal hypertension, by the prostaglandin catabolism inhibiting effect of substance 44.

The prostaglandin-A isomerase (PGAI) inhibiting action of the compounds according to the invention was measured by the method of Jones et al. (Biochim. Biophys. Acta 280, 558, 1972) on a PGAI preparation from the blood plasma of pigs, whereas the prostaglandin dehydrogenase (PGDH) inhibiting action was determined by the method of Marrazzi and Matschinsky (Prostaglandins 1, 373, 1972); on a PGDH preparation from pig lung. The PGAI and PGDH inhibiting action of several substances is shown in Table II.

Table II

| No. of Examples | $I_{50\%}$ inhibiting levels in final concentrations expressed in millimoles | |
| --- | --- | --- |
| | PGDH | PGAI |
| 17 | 0.20 | 0 |

Table II-continued

| No. of Examples | $I_{50\%}$ inhibiting levels in final concentrations expressed in millimoles | |
| --- | --- | --- |
| | PGDH | PGAI |
| 19 | 0 | 0.13 |
| 21 | 0 | 0.020 |
| 25 | 0 | 0.025 |
| 31 | 0 | 0.060 |
| 34 | 0.11 | 0 |
| 35 | 0 | 0.080 |
| 44 | 0 | 0.070 |
| Hydralazine | — | 0.09 |
| Estrone | 0.01 | — |
| Triiodothyroacetic acid | 0.005 | — |

The $I_{50\%}$, i.e. the index of inhibition, is defined as the concentration of the substance inhibiting to 50% the function of the corresponding enzyme.

SPECIFIC EXAMPLES

The invention is further illustrated by means of the following non-limiting Examples.

EXAMPLE 1

Preparation of 3-chloro-6-(3,5-dicyclopropyl-1-pyrazolyl)-pyridazine

A mixture of 5.8 g (0.04 moles) of 3-chloro-6-pyridazinylhyrazine, 6.08 g (0.04 moles) of 1,3-dicyclopropyl-1,3-popanedione and 60 ml of ethanol is heated to reflux for 5 hours, then the ethanol is removed under reduced pressure and the residue recrystallized from isopropanol. Yield: 8.15 g (78%); m.p.: 102°–105° C.

The substances prepared by the same process are shown in Table III.

Table III

| No. of Example | Chemical name of the compound | Melting point °C. | Yield* % |
| --- | --- | --- | --- |
| 2 | 3-Chloro-6-(3,5-diphenyl-1-pyrazolyl)-pyridazine | 190-2 | 87.5 |
| 3 | 3-Chloro-6-(3,5-diethyl-1-pyrazolyl)-pyridizing | 103-4 | 51 |
| 4 | 3-Chloro-6-(3,4,5-trimethyl-1-pyrazolyl)-pyridazine | 138-141 | 63 |
| 5 | 3-Chloro-6-(3,5-dimethyl-4-ethyl-1-pyrazolyl)-pyridazine | 84-5 | 56 |
| 6 | 3-Chloro-6-(3,5-dimethyl-4-isopropyl-1-pyrazolyl)-pyridazine | 68-70 | 46.5 |
| 7 | 3-Chloro-6-(3,5-dimethyl-4-phthalimido-1-pyrazolyl)-pyridazine | 222-4 | 46 |

Note to Table III:
*preparative yields

EXAMPLE 8

Preparation of 3-chloro-(3,5-dimethyl-4-chloro-1-pyrazolyl/-pyridazine

To a mixture of 10.43 g (0.05 moles) of 3-chloro-6-/3,5-dimethyl-1-pyrazolyl/-pyridazine and 100 ml of ether, 13.5 g /0.01 moles/ of sulphuryl chloride are added dropwise at 0° C. under stirring and then the mixture is stirred at 0° C. for one hour, set aside at room temperature for one hour and heated to reflux for 2 hours. After cooling the separated crystals are filtered and recrystallized from methanol. Yield: 7.85 g (64.5%); m.p. 140°–142° C.

EXAMPLE 9

Preparation of 3-chloro-6-(3,5-dimethyl-4-bromo-1-pyrazolyl)-pyridazine

A mixture of 2.09 g (0.01 moles) of 3-chloro-6-(3,5-dimethyl-1-pyrazolyl)-pyridazine, 21 ml of carbon tetrachloride and 1.96 g (0.011 moles) of N-bromosuccinimide is boiled under stirring for 3 hours. After cooling the precipitate is filtered, washed with carbon tetrachloride and recrystallized from ethanol. Yield: 1.44 g (50.5%); m.p.: 143°–145° C.

EXAMPLE 10

Preparation of 3-chloro-6-(3,5-dimethyl-4-nitro-1-pyrazolyl)-pyridazine

To a mixture of 230 ml of concentrated sulphuric acid and 230 ml of 100% nitric acid, 26 g of 3-chloro-6-(3,5-dimethyl-1-pyrazolyl)-pyridazine are added portionwise, under stirring at a temperature between 0° C. and 5° C., then the mixture is stirred at room temperature for 2 hours, poured into 1 liter of water and set aside overnight in the refrigerator. The separated crystals are filtered, washed with water and dried. Yield: 26.7 g (84.5%); m.p. 164°–167° C.

EXAMPLE 11

Preparation of 3-chloro-6-(4-nitro-1-pyrazolyl)-pyridazine

This substance is prepared according to Example 10 but 3,6 g (0.02 moles) of 3-chloro-6-(1-pyrazolyl)-pyridazine are used as starting material. Yield: 4.05 g (B 90%); m.p.: 169°–172° C.

EXAMPLE 12

Preparation of 3-chloro-6-(3,5-diethyl-4-nitro-1-pyrazolyl)-pyridazine

This substance is prepared according to Example 10 but 2.37 g (0.01 moles) of 3-chloro-6-(3,5-diethyl-1-pyrazolyl)-pyridazine are used as starting material. Yield: 1.55 g (55%); m.p.: 83°–85° C.

EXAMPLE 13

Preparation of 3-chloro-6-(3,5-dimethyl-4-amino-1-pyrazolyl)-pyridazine

A mixture of 3.54 g (0.01 moles) of 3-chloro-6-(3,5-dimethyl-4-phthalimido-1-pyrazolyl)-pyridazine, 40 ml of ethanol and 1.08 g (0.01 moles) of 98% hydrazine hydrate is heated to reflux for 3 hours and the mixture is poured into 100 ml of water. After cooling the precipitated crystals are filtered, washed with water, triturated with 10 ml of hot ethanol, filtered and dried. Yield: 1.8 g (81%); m.p. 165°–168° C.

EXAMPLE 14

Preparation of 3-chloro-6-(3-methyl-5-amino-1-pyrazolyl)-pyridazine

A mixture of 14.5 g (0.1 moles) of 3-chloro-6-pyridazinyl-hydrazine, 8.5 g (0.1 moles) of 3-iminobutyronitrile and 150 ml of ethanol is heated to reflux for 9 hours. After cooling the separated crystals are filtered, washed with ethanol and dried. Yield: 15.6 g (74.0%); m.p.: 148°–150° C. The hydrochloride melts at 157°–159° C.

EXAMPLE 15

Preparation of 3-chloro-6-(3-methyl-5-chloro-1-pyrazolyl)-pyridazine

To the mixture of 12.6 /0.04 moles/ of 3-chloro-6-(3-methyl-5-hydroxy-1-pyrazolyl)-pyridazine and 48 ml of phosphorus oxychloride, 7.28 g /0.04 moles/ of dimethyl aniline are dropped under stirring at 0° C. during half an hour, then the reaction mixture is stirred at room temperature for one hour and at boiling temperature for 2 hours. Excess of the phosphorus oxychloride is evaporated under reduced pressure, then the residue is poured into water and set aside overnight. The separated precipitate is filtered, washed with water and dried. Yield: 10.5 g (93%); m.p.: 123°–126° C.

EXAMPLE 16

Preparation of 3-benzylamino-6-(3,5-dicyclopropyl-1-pyrazolyl)-pyridazine

A mixture of 7.82 g (0.03 moles) of 3-chloro-6-(3,5-dicyclopropyl-1-pyrazolyl)-pyridazine (prepared according to Example 1) and 7.1 g (0.066 moles) of benzylamine is heated at 150° C. for 8 hours. After cooling the mixture is triturated with water, then the precipitate is filtered and recrystallized from ethanol. Yield: 4.45 g (44.7%); m.p.: 138°–140° C.

For preparation of the hydrochloride salt, the base is suspended in ether, and gaseous hydrogen chloride is introduced until saturation. The precipitate is filtered, washed with ether and dried. Yield: 4.4 g; m.p.: 178°–181° C.

(The hydrochlorides or bases were prepared according to the following Examples in a similar way.)

The substances prepared by the same process are shown in Table IV.

Table IV

| No. of Example | Chemical name of the compound | Melting point °C. | Yield* % |
| --- | --- | --- | --- |
| 17 | 3-Benzylamino-6-(3,5-dimethyl-1-pyrazolyl)-pyridazine | 172–4 | 74.5 |
| 18 | 3-[bis-(Hydroxyethyl)-amino]-6-(3,5-dimethyl-1-pyrazol)-pyridazine | 92.5 | 54 |
| 19 | 3-Dimethylamino-6-(3,5-dimethyl-1-pyrizolyl)-pyridazine | 218–221** | 94 |
| 20 | 3-Cyclopropylamino-6-(3,5-dimethyl-1-pyrazolyl)-pyridazine | 171–5 | 86.5 |
| 21 | 3-Benzylamino-6-(3,5-diphenyl-1-pyrazolyl)-pyridazine | 204–5 | 40 |
| 22 | 3-[bis-(Hydroxyethyl)-amino]-6-(3,5-:dimethyl-4-nitro-1-pyrazolyl)-pyridazine | 171–4 | 72 |
| 23 | 3-Morpholino-6-(3,5-dimethyl-4-nitro-1-pyradolyl)-pyridazine | 184–5 | 76 |
| 24 | 3-Morpholin-6-(3-methyl-5-amino-1-pyrazolyl)-pyridazine | 191–3 | 55 |

Notes to Table IV:
*preparative yields
**hydrochloride salt

EXAMPLE 25

Preparation of
3-hydrazino-6-(3,5-dimethyl-1-pyrazolyl)-pyridazine

A mixture of 34.2 g. of 3-chloro-6-(3,5-dimethyl-1-pyrazolyl)-pyridazine, 100 ml of 72% hydrazine hydrate and 200 ml of dioxane is stirred at 90°–95° C. for 14 hours, then the mixture is poured into 1 liter of water, extracted three times with 150 ml of chloroform each, and the combined organic phases are dried over magnesium sulphate. After evaporation of the solvent, the residue is recrystallized from isopropanol. Yield: 27 g /80%/; m.p.: 142°–143° C.

The substances prepared by the same process are shown in Table V.

Table V

| No. of Example | Chemical name of the compound | Melting point °C. | Yield % |
|---|---|---|---|
| 26 | 3-Hydrazino-6-(3,5-dicyclopropyl-1-pyrazolyl)-pyridazine | 125–7 175–8** | 56.5 |
| 27 | 3-Hydrazino-6-(3,5-diphenyl-1-pyradolyl)-pridazine | 223–5 | 79.5 |
| 28 | 3-Hydrazino-6-(1-pyrazolyl)-pyridazine | 188–190 | 56.5 |
| 29 | 3-Hydrazino-6-(3,5-diethyl-1-pyrazolyl)-pridazine | 128–129 155–157** | 87.5 |
| 30 | 3-Hydrazino-6-(3,5-diisopropyl-1-pyazolyl)-pridazine | oil | |
| 31 | 3-Hydrazino-6-(3,4,5-trimethyl-1-pyrazolyl)-pridazine | 152–4 237–9** | 63.0 |
| 32 | 3-Hydrazino-6-(3,5-dimethyl-4-ethyl-1-pyrazolyl)-pyridazine | 118–121 212–215** | 58.5 |
| 33 | 3-Hydrazino-6-(3,5-dimethyl-4-isopropyl-1-pyrazolyl)-pyridazine | 105–7 185–8** | 52.5 |
| 34 | 3-Hydrazino-6-(3,5-dimethyl-4-chloro-1-pyrazolyl)-pyridazine | 195–7 | 88.5 |
| 35 | 3-Hydrazini-6-(3,5-dimethyl-4-bromo-1-pyrazolyl)-pyridazine | 184–7 219–221** | 60.5 |
| 36 | 3-Hydrazino-6-(4-nitro-1-pyrazolyl)-pyridazine | 208–210 | 60.0 |
| 37 | 3-Hydrazino-6-(3,5-dimethyl-4-nitro-1-pyrazolyl)-pyridazine | 240–2 213–5** | 81.0 |
| 38 | 3-Hydrazino-6-(3,5-diethyl-4-nitro-1-pyrazolyl)-pridazine | 148–150 | 78.0 |
| 39 | 3-Hydrazin-6-(3-methyl-5-chloro-1-pyrazolyl)-pyridazine | 197–8 | 49.5 |
| 40 | 3-Hydrazino-6-(5-amino-1-pyrazolyl)-pyridazine | 208–210 | 40.0 |
| 41 | 3-Hydrazino-6-(3-methyl-5-amino-1-pyrazolyl)-pyridazine | 150–3 | 24.0 |

Notes to Table V:
*preparative yields
**hydrochloride salt

EXAMPLE 42

Preparation of
3-(1-methylhydrazino)-6-(3,5-dimethyl-1-pyrazolyl)-pyridazine

A mixture of 4.17 g (0.02 moles) of 3-chloro-6-(3,5-dimethyl-1-pyrazolyl)-pyridazine, 42 ml of ethanol and 2.3 g (0.05 moles) of methyl hydrazine is heated to reflux for 9 hours, and after cooling the mixture is poured into 100 ml of water. The solution is extracted with 3×50 ml of chloroform and the combined organic phases are dried over magnesium sulphate. After evaporation the residue is recrystallized from a 3:1 mixture of isopropanol and petroleum ether. Yield: 1.9 g (44.5%); m.p.: 93°–94° C.

EXAMPLE 43

Preparation of
3-(2-hydroxyethylhydrazino)-6-(3,5-dimethyl-1-pyrazolyl)-pyridazine A mixture of 2.09 g (0.01 moles) of 3-chloro-6-(3,5-dimethyl-1-pyrazolyl)-pyridazine, 30 ml of ethanol and 1.52 g (0.02 moles) of hydroxyethyl hydrazine is reacted and worked up in the same way as described in Example 42. Yield: 0.3 g (10.5%); the hydrochloride melts at 302°–305° C.

EXAMPLE 44

Preparation of
3-hydrazino-6-(3,5-dimethyl-4-amino-1-pyrazolyl)-pyridazine

Method "A":

A mixture of 2.54 g (0.01 moles) of 3-chloro-6-(3,5-dimethyl-4-amino-1-pyrazolyl)-pyridazine (prepared according to Example 13) and 10 ml of 98% hydrazine hydrate is stirred at 95° for 3 hours, then the mixture is poured into water. The obtained solution is continuously extracted with chloroform, the organic phase is dried, evaporated and the residue is treated with ethanolic hydrochloric acid. The separated precipitate is filtered, washed with chloroform and ether and dried. Yield: 1.33 g (45.5%) of the dihydrochloride salt; m.p. 259°–261° C.

Method "B":

The mixture of 9 g of 3-hydrazino-6-(3,5-dimethyl-4-nitro-1-pyrazolyl)-pyridazine (prepared according to Example 37) and 250 ml of methanol is hydrogenated at room temperature and normal pressure in the presence of 2 g of palladium on charcoal catalyst until consumption of the theoretical amount of hydrogen (about 16–20 hours). Then the catalyst is filtered out, washed with aqueous hydrochloric acid of 6%, the filtrate is evaporated to dryness and the residue recrystallized from aqueous ethanol. Yield: 7.4 g (70%) of the dihydrochloride salt; m.p.: 262°–264° C.

Method "C":

A mixture of 3.19 g (10 mmoles) of 3-[2-(tert-butyloxycarbonyl)-1-hydrazino]-6-(3,5-dimethyl-4-amino-1-pyrazolyl/-pyridazine (prepared according to Example 56) and 64 ml of 20% aqueous hydrochloric acid is heated to reflux for 40 minutes and then evaporated to dryness. The residue is recrystallized from ethanol. Yield: 75% of the dihydrochloride salt; m.p.: 260°–264° C.

The substances prepared according to the Method "B" of Example 44 are shown in Table VI.

Table VI

| No. of Example | Chemical name of the compound | Melting point ° C. | Yield % |
|---|---|---|---|
| 45 | 3-Hydrazino-6-(4-amino-1--pyrazolyl)-pyridazine | 240–4** | 50 |
| 46 | 3-Hydrazino-6-(3,5-diethyl-4-amino-1-pyrazolyl)--pyridazine | 242–245** | 44 |
| 47 | 3-Hydrazino-6-(3,5-diisopropyl-4-amino-1-pyrazolyl)-pyridazine | oil | |
| 48 | 3-Morpholino-6-(3,5-dimethyl-4-amino-1-pyrazolyl)- | 223–228** | 28.5 |

Table VI-continued

| No. of Example | Chemical name of the compound | Melting point °C. | Yield % |
|---|---|---|---|
| | -pyridazine | | |

Notes to Table VI:
*preparative yields
**dihydrochloride salt

EXAMPLE 49

Preparation of
3-morpholino-6-(3,5-dimethyl-1-pyrazolyl)-pyridazine

A mixture of 1.95 g (0.01 moles) of 3-morpholino-6-pyridazinylhydrazine, 1.0 g (0.01 moles) of acetylacetone and 20 ml of ethanol is heated to reflux for 3 hours. After cooling the separated crystals are filtered, washed with ethanol and dried. Yield: 1.65 g (64.5%); m.p. 119°–121° C.

EXAMPLE 50

3-Morpholino-6-(3-methyl-5-hydroxy-1-pyrazolyl)-pyridazine

A mixture of 0.98 g (5 mmoles) of 3-morpholino-6-pyridazinyl-hydrazine, 0.65 g (5 mmoles) of ethyl acetoacetate and 15 ml of ethanol is stirred at reflux temperature for 3 hours. After cooling the mixture is stirred with 1 ml of concentrated aqueous ammonium hydroxide solution at room temperature for 4 hours and then left to stand overnight. The separated crystals are filtered, washed with water and recrystallized from ethanol. Yield: 0.5 g (39%); m.p.: 189°–192° C.

EXAMPLE 51

Preparation of
3-carbamoyl-6-(3,5-dimethyl-1-pyrazolyl)-pyridazine

A mixture of 1.53 g (0.01 moles) of 3-carbamoyl-6-pyridazinyl-hydrazine, 1.1 g (0.011 moles) of acetylacetone and 15 ml ethanol is heated to reflux under stirring for 3 hours. After cooling the separated crystals are filtered, washed with ethanol and dried. Yield: 2.05 g (95%); m.p.: 256°–257° C.

EXAMPLE 52

Preparation of
3-cyano-6-(3,5-dimethyl-1-pyrazolyl)-pyridazine

This substance is prepared according to Example 51 but 1.35 g (0.01 moles) of 3-cyano-6-pyridazinylhydrazine are used as starting material. Yield: 1.38 g (69.5%); m.p.: 187°–189° C.

EXAMPLE 53

Preparation of
3-(1-ethoxycarbonyl-1-hydrazino(-6-(3,5-dimethyl-1-pyrazolyl)pyridazine A mixture of 4.08 g (0.02 moles) of 3-hydrazino-6-(3,5-dimethyl-1-pyrazolyl)-pyridazine, 60 ml of dichloroethane and 4.86 g (0.03 moles) of diethyl pyrocarbonate is stirred at room temperature for 24 hours. The precipitated crystals are filtered to give 2.6 g of 3-(2-ethoxycarbonyl-1-hydrazino)-6-(3,5-dimethyl-1-pyrazolyl)-pyridazine; m.p.: 168°–170° C. After evaporation of the filtrate, the residue is treated with a mixture of ethyl acetate and petroleum ether. The precipitate is filtered, washed and dried. Yield: 0.4 g (7%); m.p.: 124°–127° C. The 4-nitrophenyl hydrazone of the substance melts at 205°–208° C.

EXAMPLE 54

Preparation of
3-(2-ethoxycarbonyl-1-hydrazino-)-6-(3,5-dimethyl-1-pyrazolyl)-pyridazine To a mixture of 6.12 g (0.03 moles) of 3-hydrazino-6-(3,5-dimethyl-1-pyrazolyl)-pyridazine and 60 ml of pyridine, 3.6 g (0.033 moles) of ethyl chloroformate are dropped under stirring at 0° C. Then the mixture is stirred at room temperature for 3 hours, left to stand overnight and treated with 10% hydrochloric acid until neutral. The separated product is extracted with chloroform and the solution is dried over magnesium sulphate. After evaporation of the solvent the residue is recrystallized from ethanol. Yield: 2.85 g (34.5%); m.p.: 169°–171° C.

EXAMPLE 55

Preparation of
3-(2-tert-butoxycarbonyl-1-hydrazino)-6-(3,5-dimethyl-4-nitro-1-pyrazolyl)-pyridazine A mixture of 2.29 g (9 mmoles) of 3-chloro-6-(3,5-dimethyl-4-nitro-1-pyrazolyl)-pyridazine (prepared according to Example 10) and 2.64 g (20 mmoles) of tert-butoxycarbonyl-hydrazine is heated at 130° C. for 2 hours. After cooling the mixture is triturated with 25 ml of water, filtered and the precipitate is recrystallized from 40 ml of ethanol. Yield: 1.95 g (59%); m.p.: 196°–198° C.

EXAMPLE 56

Preparation of
3-(2-tert-butoxycarbonyl-1-hydrazino)-6-(3,5-dimethyl-4-amino-1-pyrazolyl)-pyridazine This substance is prepared according to the Method "B" of Example 44 but 3.5 g (10 mmoles) of 3-(2-tertiary-butoxycarbonyl-1-hydrazino)-6-(3,5-dimethyl-4-nitro-1-pyrazolyl)-pyridazine (prepared according to Example 55) are used as starting material. Yield: 1.65 g (51.5%); m.p.: 195°–198° C.

EXAMPLE 57

Preparation of
3-(2-tert-butoxycarbonyl-1-hydrazino)-6-(3,5-dimethyl-4-bis[hydroxyethyl]-amino-1-pyrazolyl)-pyridazine A mixture of 3.2 g (0.01 moles) of 3-(2-tertiary-butoxycarbonyl-1-hydrazino)-6-(3,5-dimethyl-4-amino-1-pyrazolyl)-pyridazine (prepared according to Example 56), 32 ml of tetrahydrofurane and 4.4 g (0.1 moles) of ethylene oxide is shaken at atmospheric pressure in a closed tube for 24 hours. After evaporation of the volatile materials the residue is dissolved in 50 ml of dichloromethane, washed with 2×15 ml of water and dried over magnesium sulphate. After evaporation of the solvent, 2.9 g (79%) of an oily product are obtained.

EXAMPLE 58

Tablets containing 200 mg of active ingredient each, for oral use and therapeutic purposes are prepared from the following components:

| | | |
|---|---|---|
| 3-Hydrazino-6-(3,5-dimethyl) -4-amono-1-pyrazolyl)- pyridazine | 200 | mg |

| | | |
|---|---|---|
| Microcrystalline cellulose | 146.4 | mg |
| Colloidal silicon dioxide | 1.8 | mg |
| Magnesium stearate | 1.8 | mg |

The average weight of one tablet is 350 mg.
The tablets are covered with film coat.

For parenteral use, a sterile, frozen-dried product conaining in each ampoule 25 mg of 3-hydrazino-6-(3,5-dimethyl-4-amino-1-pyrazolyl)-pyridazine dihydrochloride is prepared from the solution of the compound (in injectable distilled water).

What we claim is:

1. A compound of the formula I

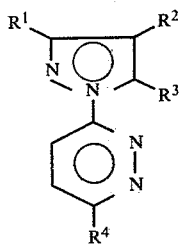

wherein
$R^1$ is hydrogen, $C_{1-6}$ alkyl, $C_{2-4}$ hydroxyalkyl, $C_{3-6}$ cycloalkyl or phenyl;
$R^2$ is hydrogen, fluorine, chlorine, bromine, $C_{1-6}$ alkyl, $C_{2-4}$ hydroxyalkyl, nitro, or —$NR^5R^6$, wherein $R^5$ and $R^6$ are the same or different and each is hydrogen, $C_{1-4}$ alkyl or $C_{2-4}$ hydroxyalkyl;
$R^3$ is hydrogen, $C_{1-6}$ alkyl, $C_{2-4}$ hydroxyalkyl, $C_{3-6}$ cycloalkyl, phenyl, chlorine, hydroxyl, amino or methoxy;
$R^4$ is carbamoyl, cyano, —$NR^7$—$NHR^8$, or —$NR^9R^{10}$ and wherein: $R^7$ and $R^8$ are the same or different and each is hydrogen, $C_{1-4}$ alkyl, $C_{2-4}$ hydroxyalkyl, or $C_{1-4}$ alkoxycarbonyl; and $R^9$ and $R^{10}$ are the same or different and each is hydrogen, $C_{1-5}$ alkyl, $C_{2-4}$ hydroxyalkyl, $C_{3-6}$ cycloalkyl, phenyl or benzyl; or —$NR^9R^{10}$ is a morpholine, piperidine or piperazine ring, or a pharmaceutically acceptable acid-addition salt of the compound of formula I.

2. The compound defined in claim 1 which is 3-hydrazino-6-(3,4,5-trimethyl-1-pyrazolyl)-pyridazine or a pharmaceutically acceptable acid addition salt thereof.

3. The compound defined in claim 1 which is 3-hydrazino-6-(3,5-dimethyl-4-amino-1-pyrazolyl)-pyridazine or a pharmaceutically acceptable acid-addition salt thereof.

4. The compound defined in claim 1 which is 3-(2-tertiary-butoxycarbonyl-1-hydrazino)-6-(3,5-dimethyl-4-amino-1-pyrazolyl)-pyridazine or a pharmaceutically acceptable acid-addition salt thereof.

5. The compound defined in claim 1 which is 3-hydrazino-6-(3,5-diethyl-4-amino-1-pyrazolyl)-pyridazine or a pharmaceutically acceptable acid-addition salt thereof.

6. The compound defined in claim 1 which is 3-hydrazino-6-(4-amino-1-pyrazolyl)-pyridazine or a pharmaceutically accpetable acid-addition salt thereof.

7. The compound defined in claim 1, which is 3-hydrazino-6-(5-amino-1-pyrazolyl)-pyridazine or a pharmaceutically acceptable acid-addition salt thereof.

8. The compound defined in claim 1 which is 3-hydrazino-6-(3,5-diethyl-1-pyrazolyl)-pyridazine or a ppharmaceutically acceptable acid-addition salt thereof.

9. The compound defined in claim 1 which is 3-hydrazino-6-(3,5-dicyclopropyl-1-pyrazolyl)-pyridazine or a pharmaceutically acceptable acid-addition salt thereof.

10. The compound defined in claim 1 which is 3-hydrazino-6-(3,5-dimethyl-1-pyrazolyl)-pyridazine or a pharmaceutically acceptable acid-addition salt thereof.

11. The compound defined in claim 1 which is 3-hydrazino-6-(3,5-dimethyl-4-chloro-1-pyrazolyl)-pyridazine or a pharmaceutically acceptable acid-addition salt thereof.

12. A pharmaceutical composition of hypotensive and prostaglandin catabolism inhibiting activity, containing as an active ingredient a compound of formula I as defined in claim 1, in association with a pharmaceutically acceptable and inert further ingredient.

* * * * *